US009388397B2

(12) United States Patent
Rosenblum et al.

(10) Patent No.: US 9,388,397 B2
(45) Date of Patent: Jul. 12, 2016

(54) DEIMMUNIZED GELONIN MOLECULES AND THERAPIES

(71) Applicant: Research Development Foundation, Carson City, NV (US)

(72) Inventors: Michael G. Rosenblum, Sugar Land, TX (US); Lawrence Cheung, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 14/767,745

(22) PCT Filed: Feb. 14, 2014

(86) PCT No.: PCT/US2014/016432
§ 371 (c)(1),
(2) Date: Aug. 13, 2015

(87) PCT Pub. No.: WO2014/127211
PCT Pub. Date: Aug. 21, 2014

(65) Prior Publication Data

US 2015/0368628 A1 Dec. 24, 2015

Related U.S. Application Data

(60) Provisional application No. 61/765,380, filed on Feb. 15, 2013.

(51) Int. Cl.

| | |
|---|---|
| ***C12N 9/24*** | (2006.01) |
| ***A61K 47/48*** | (2006.01) |
| ***C07K 14/41*** | (2006.01) |
| ***A61K 38/47*** | (2006.01) |
| ***C07K 14/415*** | (2006.01) |
| ***A61K 45/06*** | (2006.01) |
| ***C12N 9/96*** | (2006.01) |
| *A61K 38/16* | (2006.01) |

(52) U.S. Cl.
CPC . *C12N 9/24* (2013.01); *A61K 38/47* (2013.01); *A61K 45/06* (2013.01); *A61K 47/48246* (2013.01); *C07K 14/415* (2013.01); *C12N 9/96* (2013.01); *A61K 38/168* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 5,191,066 | A | 3/1993 | Bieniarz et al. | |
| 5,631,348 | A * | 5/1997 | Rosenblum | C07K 14/415 530/370 |
| 5,837,491 | A * | 11/1998 | Better | A61K 47/48469 435/252.3 |
| 7,083,957 | B2 * | 8/2006 | Rosenblum | C07K 14/415 435/183 |

FOREIGN PATENT DOCUMENTS

| | | |
|---|---|---|
| WO | WO 02/069886 | 9/2002 |
| WO | WO 03/103715 | 12/2003 |
| WO | WO 2005/090579 | 9/2005 |

OTHER PUBLICATIONS de Virgilio et al., "Ribosome-inactivating proteins: from plant defense to tumor attack," *Toxins*, 2(11):2699-2737, 2010.
Luster et al., "Fusion toxin BLyS-gelonin inhibits growth of malignant human B cell lines in vitro and in vivo," *PLoS One*, 7(10):e47361, 2012.
PCT International Preliminary Report on Patentability issued in International Application No. PCT/US2014/016432, mailed Aug. 27, 2015.
PCT International Search Report and Written Opinion issued in International Application No. PCT/US2014/016432, mailed Jul. 29, 2014.
Roscoe et al., "Primate antibody response to immunotoxin: serological and computer-aided analysis of epitopes on a truncated form of *Pseudomonas* exotoxin," *Infection and Immunity*, 62(11):5055-5065, 1994.
Sairam et al., "Structural characterization of gelonin: evidence for separate antigenic and cytotoxic domains," *Biochemistry and Molecular Biology International*, 31(3):575-581, 1993.

* cited by examiner

*Primary Examiner* — Suzanne M Noakes
(74) *Attorney, Agent, or Firm* — Parker Highlander PLLC

(57) ABSTRACT

Recombinant gelonin polypeptides with decreased antigenicity are provided. Cell-targeted constructs comprising said recombinant gelonin polypeptides are also provided. Such constructs can be used in methods for targeted cell killing, such as for treatment of cell proliferative diseases (e.g., cancer).

20 Claims, 3 Drawing Sheets

```
FMH     GLDTVSFSTKGATYITYVNALNELRVKNQWDGTQHGVELLRKKCDDPGKCFVLVALSNDN 60
SDH     GLDTVSFSTK--------------RVKNQWDGTQHGVELLRKKCDDPGKCFVLVALSNDN 46
rGel    GLDTVSFSTKGATYITYVNFLNELRVKLKPEGNSHGIPLLRKKCDDPGKCFVLVALSNDN 60
        **********              *** : :*..**: **********************

FMH     GQLAEIAIDVTSIYIVGIQARNEVLFYRDAPDAAFEGLGKNTIKTRLHFGGSYPSLEGEK 120
SDH     GQLAEIAIDVTSIYIVGIQARNEKLFYR---------------------GGSYPSLEGEK 85
rGel    GQLAEIAIDVTSVYVVGYQVRNRSYFFKDAPDAAYEGLFKNTIKTRLHFGGSYPSLEGEK 120
        ***********:*:** *.**.  *::                      ***********

FMH     AYRETTDLGIEPLRIGIKKLDENAIDNYKPTEIASSLLVVIQLVSEAARFTFIENQLRNN 180
SDH     AYRETTDLGIEPLRIGIKKLDENAIDNYKPTEIASSLLVVIQSVSEAARFTFIENQLRNN 145
rGel    AYRETTDLGIEPLRIGIKKLDENAIDNYKPTEIASSLLVVIQMVSEAARFTFIENQIRNN 180
        ****************************************** *************:***

FMH     FQQRVSEENETTSYEGKWGKLSFQIRTSGANGMFSEAVELERANGKKYYVTAVDQVKPKI 240
SDH     FQQRVSEENETTSYEGKWGK---------------------------------------- 165
rGel    FQQRIRPANNTISLENKWGKLSFQIRTSGANGMFSEAVELERANGKKYYVTAVDQVKPKI 240
        ****:    *:* * *.****

FMH     ALLKFVDKDPK 251
SDH     ----------- 165
rGel    ALLKFVDKDPK 251
```

FIG. 1

DEIMMUNIZED GELONIN MOLECULES AND THERAPIES

The present application is a national phase application under 35 U.S.C. §371 of International Application No. PCT/US2014/016432, filed Feb. 14, 2014, which claims the priority benefit of U.S. provisional application No. 61/765,380, filed Feb. 15, 2013, the entire contents of each of which are incorporated herein by reference.

BACKGROUND OF THE INVENTION

1. Field of the Invention

The present invention relates generally to the field of molecular biology and recombinant protein production. More particularly, it concerns gelonin polypeptides with decreased immunogenicity and cell-targeting constructs comprising said less immunogenic gelonin polypeptides.

2. Description of Related Art

The successful development of targeted therapeutics (e.g., for cancer applications) depends on the identification of ligands and antigens specific for target cells, generation of molecules capable of targeting those components specifically and, finally, use of highly toxic molecules for killing of target cells. Immunoconjugates composed of antibodies and small, toxic drugs or radioisotopes have been successfully tested in vitro, in animal models and have demonstrated activity in the clinical setting. In addition to the use of small molecules for the toxin component, a number of highly cytotoxic protein components, such as diphtheria toxin, ricin A-chain, *Pseudomonas* exotoxin, and gelonin (rGel), have been used for targeted therapies. However, problems such as capillary leak syndrome, immunogenicity, and inadvertent toxicity (to non-targeted cells) continue to limit implementation of successful therapy, especially for long-term or chronic applications. An immune response to the compounds can reduce, or altogether eliminate, the benefits that can be achieved through their use. Thus, there remains a need for highly specific, highly active, and non-immunogenic toxin molecules and cell-targeting constructs comprising such molecules.

SUMMARY OF THE INVENTION

In certain embodiments, the present invention provides recombinant gelonin toxin that is altered with respect to the native gelonin sequence. The recombinant gelonin toxin may have amino acids replaced or removed as compared to the native gelonin protein sequence (shown in SEQ ID NO: 12), which is disclosed in U.S. Pat. No. 5,631,348, which is herein incorporated by reference and which is provided by GenBank accession number L12243.

In one aspect, the recombinant gelonin toxin has a sequence according to SEQ ID NO: 1. In another aspect, the recombinant gelonin toxin has a sequence according to SEQ ID NO: 2. The recombinant gelonin toxins may be comprised within a recombinant polypeptide. In some aspects, the recombinant polypeptide comprising a recombinant gelonin toxin of the present invention may be fused to a second polypeptide to form a fusion protein. The recombinant gelonin and the second polypeptide may be separated by a linker, for example, a $G_4S$, $(G_4S)2$, $(G_4S)3$, 218 linker, enzymatically cleavable linker, or pH cleavable linker. In other aspects, the recombinant gelonin toxin and the second polypeptide may be conjugated.

In certain aspects of the present invention, the second polypeptide may be a cell binding moiety. The cell binding moiety may be an antibody or immunoglobulin chain, such as, a monoclonal antibody, human antibody, humanized antibody, deimmunized antibody, chimeric antibody, Fab', Fab, F(ab')2, single domain antibody, Fv, or single chain Fv (scFv) antibody. The cell binding moiety may bind to a protein, carbohydrate, or lipid expressed on cancer cells. Examples of proteins that the cell binding moiety may bind include, but are not limited to, BLyS, GP240, 5T4, HER1, HER2, CD-33, CD-38, Flt-1, Flk-1, CEA, FGFR3, IGFBP2, or IGF-1R. The cell binding moiety may be $VEGF_{121}$. When the cell binding moiety is $VEGF_{121}$, then the recombinant polypeptide may comprise the sequence of SEQ ID NO: 3 or SEQ ID NO: 4.

In certain embodiments, the present invention provides polynucleotides that comprise a nucleic acid sequence encoding a recombinant polypeptide comprising SEQ ID NOs: 1 or 2. In additional embodiments, the present invention provides host cells that comprise said polynucleotide that encodes a recombinant polypeptide comprising SEQ ID NOs: 1 or 2. In some aspects, the host cell may express the polypeptide. In certain aspects, the host cell is a mammalian cell, a yeast cell, a bacterial cell, a ciliate cell, or an insect cell.

Another embodiment of the present invention provides a method of treating a cell proliferative disease in a subject comprising administering to the subject an effective amount of a polypeptide comprising a recombinant gelonin according to SEQ ID NOs: 1 or 2 and a cell binding moiety that specifically targets a diseased cell, thereby killing or inhibiting the diseased cell. In certain aspects, the method may further comprise administering to the subject chemotherapy, radiotherapy, gene therapy, or a second immunotherapy.

In certain aspects, the polypeptide is administered to the subject by administering an expression construct capable of expressing the polypeptide. The expression construct may be a viral vector, such as, for example, an adenovirus vector, an adeno-associated virus vector, a hepatitis virus, a herpesvirus, a lentivirus, a retrovirus, or a vaccinia virus.

One embodiment of the present invention provides a composition comprising a recombinant polypeptide comprising a recombinant gelonin sequence according to SEQ ID NOs: 1 or 2. The recombinant polypeptide may further comprise a cell binding moiety, such as, for example, $VEGF_{121}$. The recombinant polypeptide may comprise the sequence of SEQ ID NOs: 2 or 4. The composition may further comprise a pharmaceutically acceptable carrier.

In one embodiment, the present invention provides a composition comprising a recombinant polypeptide comprising a recombinant gelonin toxin according to SEQ ID NO: 1 or SEQ ID NO: 2 for use in the treatment of a cell proliferative disease in a subject, wherein the polypeptide comprises a cell binding moiety that specifically targets a diseased cell, and wherein treatment kills or inhibits the diseased cell. In one aspect, the composition may further comprise a chemotherapeutic, radiotherapeutic, gene therapy, or an immunotherapeutic agent. In some aspects, the polypeptide may be in a pharmaceutically acceptable composition.

In one embodiment, the present invention provides the use of a recombinant polypeptide comprising a recombinant gelonin toxin according to SEQ ID NO: 1 or SEQ ID NO: 2 in the manufacture of a medicament for the treatment of a cell proliferative disease in a subject, wherein the polypeptide comprises a cell binding moiety that specifically targets a diseased cell, and wherein treatment kills or inhibits the diseased cell.

In one embodiment, the present invention provides a composition comprising a nucleic acid expression construct capable of expressing a recombinant polypeptide comprising a recombinant gelonin toxin according to SEQ ID NO: 1 or SEQ ID NO: 2 for use in the treatment of a cell proliferative disease in a subject, wherein the polypeptide comprises a cell binding moiety that specifically targets a diseased cell, and wherein treatment kills or inhibits the diseased cell. In one aspect, the composition may further comprise a chemotherapeutic, radiotherapeutic, gene therapy, or an immunotherapeutic agent. In some aspects, the nucleic acid expression construct may be in a pharmaceutically acceptable composition.

In some aspects, the expression construct may be a viral vector, such as an adenovirus vector, an adeno-associated virus vector, a hepatitis virus, a herpesvirus, a lentivirus, a retrovirus, or a vaccinia virus.

In one embodiment, the present invention provides the use of a nucleic acid expression construct capable of expressing a recombinant polypeptide comprising a recombinant gelonin toxin according to SEQ ID NO: 1 or SEQ ID NO: 2 in the manufacture of a medicament for the treatment of a cell proliferative disease in a subject, wherein the polypeptide comprises a cell binding moiety that specifically targets a diseased cell, and wherein treatment kills or inhibits the diseased cell.

In some aspects of the present embodiments, the cell proliferative disease may be a cancer, for example, a prostate, lung, brain, skin, liver, breast, lymphoid, stomach, testicular, ovarian, pancreatic, bone, bone marrow, head and neck, cervical, esophagus, eye, gall bladder, kidney, adrenal glands, heart, colon, or blood cancer. The cell binding moiety may bind a tumor antigen, such as, for example, $VEGF_{121}$. In some aspects, the diseased cell may be a cancer cell or a tumor vasculature cell.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, “a” or “an” may mean one or more. As used herein in the claim(s), when used in conjunction with the word “comprising,” the words “a” or “an” may mean one or more than one.

The use of the term “or” in the claims is used to mean “and/or” unless explicitly indicated to refer to alternatives only or the alternatives are mutually exclusive, although the disclosure supports a definition that refers to only alternatives and “and/or.” As used herein “another” may mean at least a second or more.

Throughout this application, the term “about” is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: A graphical sequence alignment of designer gelonin (FMH—SEQ ID NO: 1 and SDH—SEQ ID NO: 2) versus native gelonin (rGel—SEQ ID NO: 11). Italicized letters represent the humanized antigenic domain. Letters with a gray background represent antigenic residues. Bold letters represent sites of 25 antigenic hot spot replacement. White letters with a black background represent unchanged antigenic residues.

DESCRIPTION OF ILLUSTRATIVE EMBODIMENTS

Figure 2:
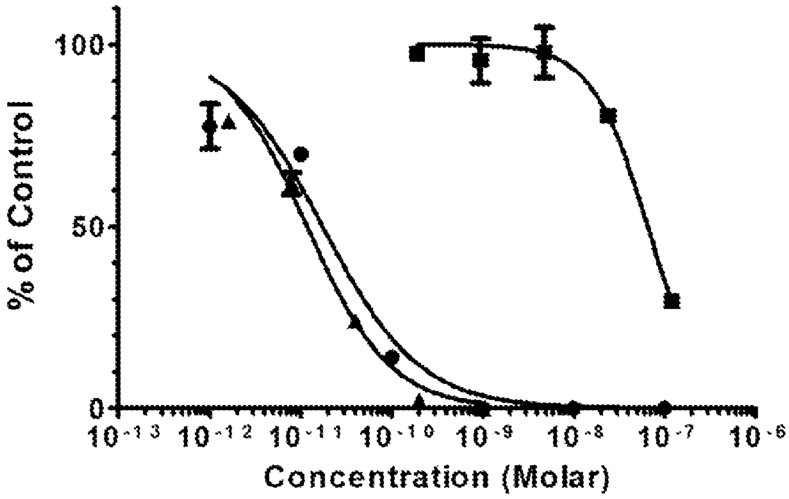
FIG. 2: In vitro activity of the VEGF-FMH. Rabbit reticulocyte lysate assays were used to determine the ability of VEGF-FMH, VEGF-rGel, and rGel to inhibit translation in a cell-free system. Circles: VEGF-rGel; squares: VEGF-FMH; triangles: rGel.

Proteins and polypeptides with reduced antigenicity can provide tremendous benefits as compositions administered to an organism with an immune system. Ribosome-inactivating proteins (RIPs), such as the plant toxin gelonin, are an example of such proteins. Proteins may be designed to provide the toxic function of one polypeptide in a combination with another polypeptide, such as a targeting molecule. These designer toxins have a wide variety of applications.

Recently, targeted cancer therapies have been developed for treating various malignancies. By virtue of their cell targeting specificity these agents can be both more effective and result in fewer side effects as compared to conventional therapy, such as chemotherapy. However, such agents can have immunogenic side effects. New therapeutics provided herein address this deficiency by providing cell-targeting constructs that are highly toxic and highly specific to targeted cell populations while being less antigenic.

In certain embodiments, the present invention concerns novel compositions comprising a proteinaceous molecule that has been modified relative to a native or wild-type protein. In some embodiments that proteinaceous compound has been deleted of amino acid residues; in other embodiments, amino acid residues of the proteinaceous compound have been replaced; while in still further embodiments both deletions and replacements of amino acid residues in the proteinaceous compound have been made. Furthermore, a proteinaceous compound may include an amino acid molecule comprising more than one polypeptide entity.

Thus, in some embodiments a designer gelonin (dGel) polypeptide having decreased immunogenicity is provided. In some aspects, such dGel polypeptides can be conjugated or fused to a cell-targeting moiety, such as VEGF, thereby providing a highly specific targeted cytotoxic construct. In such aspects, a method of targeted cancer therapy is provided that allows for specific targeted killing of cancer cells that express a given antigen while other cells are left intact. In preferred aspects, the dGel polypeptide and/or the targeting moiety are comprised of an amino acid sequence that does not produce a robust immune response when administered to a human subject.

I. Fusion Proteins And Conjugates

The present invention concerns a proteinaceous compound that may include amino acid sequences from more than one polypeptide. A proteinaceous compound or molecule, for example, could include a modified toxin with an antigen binding region of an antibody. The multipolypeptide proteinaceous molecule may be two or more proteins chemically conjugated to one another or it may be a fusion protein of two or more polypeptides encoded by the same nucleic acid molecule. Thus, a multipolypeptide proteinaceous compound may be comprised of all or part of a first polypeptide and all or part of a second polypeptide, a third polypeptide, a fourth polypeptide, a fifth polypeptide, a sixth polypeptide, a seventh polypeptide, an eight polypeptide, a ninth polypeptide, a tenth polypeptide, or more polypeptides.

Designer toxins themselves in general, have no capability to bind to the cell surface or internalize within specific cells. Therefore, these agents require either chemical conjugation to or fusion with agents/proteins that are capable of binding to specific target cells and internalizing into the cell efficiently once bound. Table 1 provides a list of proteins and polypeptides that may be conjugated or fused to toxins of the present invention, particularly in embodiments involving targeting the engineered proteinaceous compounds to a particular place, such as specific cell types or parts of the body. It is contemplated that the invention includes, but is not limited to, the examples provided in Table 1.

TABLE 1

| Genus | Subgenus | Species | Sub-species |
|---|---|---|---|
| 1) Antibodies | Polyclonal | | |
| | Monoclonal | non-recombinant | |
| | | recombinant | |
| | | | chimeric |
| | | | single chain |
| | | | diabody |
| | | | multimeric |
| 2) Cytokines/ Lymphokines/ Growth Factors | Interleukins | IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19 | |
| | EGF | | |
| | Colony Stimulating Factors (CSF) | GM-CSF, G-CSF, M-CSF | |
| | Fibroblast Growth Factors (FGF) | | |
| | LIF | | |
| | VEGF | | |
| 3) Small Chemical That Bind Cell Surface and Are Internalized | Nicotine | | |
| | ATP | | |
| | Amino Acids | | |
| | Dopamine | | |

A. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope or other tag, to facilitate targeting or purification of the fusion protein. The use of 6×His and GST (glutathione S transferase) as tags is well known. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals, or transmembrane regions.

Immunotoxins are contemplated as an embodiment of the present invention. An immunotoxin is a cytotoxic compound comprising at least a portion of an antibody and a portion of a toxin molecule. The antibody and the toxin may be fused or conjugated to each other.

In certain embodiments of the present invention, toxic polypeptides are produced as fusion proteins with cell targeting polypeptides, for example, $VEGF_{121}$, as described within the present specification. Furthermore, proteinaceous compositions of the present invention can include fusions with cell penetrating and/or membrane translocation peptides. As used herein the terms “cell penetrating peptide” and “membrane translocation domain” are used interchangeably and refer to segments of polypeptide sequence that allow a polypeptide to cross the cell membrane (e.g., the plasma membrane in the case a eukaryotic cell). Examples of CPP segments include, but are not limited to, segments derived from HIV Tat (e.g., GRKKRRQRRRPPQ; SEQ ID NO: 18), herpes virus VP22, the *Drosophila Antennapedia homeobox* gene product, protegrin I, Penetratin (RQIKIWFQNRRMKWKK; SEQ ID NO: 16), or melittin (GIGAVLKVLTTGLPALISWIKRKRQQ; SEQ ID NO: 17). In certain aspects the CPP comprises the T1 (TKIESLKEHG; SEQ ID NO: 19), T2 (TQIENLKEKG; SEQ ID NO: 20), 26 (AALEALAEALEALAEALEALAEAAAA; SEQ ID NO: 22), or INF7 (GLFEAIEGFIENGWEGMIEGWYGCG; SEQ ID NO: 21) CPP sequence.

B. Conjugated Proteins

The present invention further provides conjugated polypeptides, such as translated proteins, polypeptides and peptides, generally of the monoclonal type, that are linked to at least one agent to form a conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, anti-tumor agents, therapeutic enzymes, radio-labeled nucleotides, antiviral agents, chelating agents, cytokines, growth factors, and oligo- or polynucleotides. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a cytotoxic or anticellular agent, and may be termed “immunotoxins.” Any antibody of sufficient selectivity, specificity, or affinity may be employed as the basis for an antibody conjugate. Such properties may be evaluated using conventional immunological screening methodology known to those of skill in the art. Sites for binding to biologically active molecules in the antibody molecule, in addition to the canonical antigen binding sites, include sites that reside in the variable domain that can bind pathogens, B-cell superantigens, the T cell co-receptor CD4, and the HIV-1 envelope. In addition, the variable domain is involved in antibody self-binding and contains epitopes (idiotopes) recognized by anti-antibodies.

Molecules containing azido groups may also be used to form covalent bonds to proteins through reactive nitrene intermediates that are generated by low intensity ultraviolet light. In particular, 2- and 8-azido analogues of purine nucleotides have been used as site-directed photoprobes to identify nucleotide binding proteins in crude cell extracts. The 2- and 8-azido nucleotides have also been used to map nucleotide binding domains of purified proteins and may be used as antibody binding agents.

Several methods are known in the art for the attachment or conjugation of an antibody to its conjugate moiety. Some attachment methods involve the use of a metal chelate complex employing, for example, an organic chelating agent, such a diethylenetriaminepentaacetic acid anhydride (DTPA); ethylenetriaminetetraacetic acid; N-chloro-p-toluenesulfonamide; and/or tetrachloro-3α-6α-diphenylglycouril-3, attached to the antibody (U.S. Pat. Nos. 4,472,509 and 4,938,948, each incorporated herein by reference). Monoclonal antibodies may also be reacted with an enzyme in the presence of a coupling agent, such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers, such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region is also contemplated. This approach has been reported to produce diagnostically and therapeutically promising antibodies that are currently in clinical evaluation.

C. Linkers

A variety of linker can be used in dGel constructs of the embodiments. In some aspects a linker can be a random string of one or more amino acids (e.g., 2, 3, 4, 5, 10, 15, 20 or more amino acids). Some specific linkers for use according the embodiments include the 218 (GSTSGSGKPGSGEGSTKG; SEQ ID NO: 13), the HL (EAAAK; SEQ ID NO: 14) and the $G_4S$ (GGGGS; SEQ ID NO: 15) linkers (e.g., Robinson and Sauer, 1998; Arai et al., 2004 and Whitlow et al., 1993, each incorporated herein by reference).

In further aspects, a linker can serve as a way of separating different domains of a polypeptide construct, such as by proteolytic cleavage. For example, a linker region may comprise a protease cleavage site, such as the cleavage site recognized by an endogenous intracellular protease. In still further aspects, a protease cleavage site can be a site that is only cleaved in certain cell types (e.g., a site cleaved by a viral protease, such as HIV protease, which is only cleaved in infected cells). Examples of protease cleavage site for use according to the embodiments include, without limitation, thrombin, furin (Goyal et al., 2000), and caspase cleavage sites.

The cell targeting constructs of the embodiments may be joined by a variety of conjugations or linkages that have been previously described in the art. In one example, a biologically-releasable bond, such as a selectively-cleavable linker or amino acid sequence may be used. For instance, peptide linkers that include a cleavage site for an enzyme preferentially located or active within a tumor environment are contemplated. For example, linkers that are cleaved by urokinase, plasmin, thrombin, Factor IXa, Factor Xa, or a metalloproteinase, such as collagenase, gelatinase, or stromelysin. In a preferred embodiment, a linker that is cleaved by an intracellular proteinase is preferred, since this will allow the targeting construct to be internalized intact into targeted cells prior to cleavage.

Amino acids such as selectively-cleavable linkers, synthetic linkers, or other amino acid sequences such as the glycine rich linkers are described above and may be used to separate proteinaceous components. Additionally, while numerous types of disulfide-bond containing linkers are known that can successfully be employed to conjugate the dGel with a cell targeting moiety, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

D. Coupling Agents

Additionally, any other linking/coupling agents and/or mechanisms known to those of skill in the art can be used to combine the components of the present embodiments, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

Cross-linking reagents are used to form molecular bridges that tie together functional groups of two different molecules, e.g., a stablizing and coagulating agent. To link two different proteins in a step-wise manner, hetero-bifunctional cross-linkers can be used that eliminate unwanted homopolymer formation.

It is contemplated that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane. The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions.

Bifunctional cross-linking reagents have been extensively used for a variety of purposes including preparation of affinity matrices, modification and stabilization of diverse structures, identification of binding sites, and structural studies. In the context of the invention, such cross-linker may be used to stabilize the polypeptide or to render it more useful as a therapeutic, for example, by improving the modified protein's targeting capability or overall efficacy. Cross-linkers may also be cleavable, such as disulfides, acid-sensitive linkers, and others. Homobifunctional reagents that carry two identical functional groups proved to be highly efficient in inducing cross-linking between identical and different macromolecules or subunits of a macromolecule, and linking of polypeptides to specific binding sites on binding partners. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars. Table 2 details certain hetero-bifunctional cross-linkers considered useful in the present invention.

TABLE 2

HETERO-BIFUNCTIONAL CROSS-LINKERS

| Linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

In instances where a particular polypeptide, such as gelonin, does not contain a residue amenable for a given cross-linking reagent in its native sequence, conservative genetic or synthetic amino acid changes in the primary sequence can be utilized.

II. Antibodies

In certain embodiments, the present invention involves antibodies. For example, all or part of a monoclonal, single chain, or humanized antibody may be chemically conjugated or recombinantly fused to another proteinaceous compound such as a modified gelonin toxin. Alternatively, other aspects of the invention involve recognizing an immune response, that is, an antibody response, to a particular antigen or antigenic region in order to design and/or prepare a proteinaceous compound with less immunogenicity than a native form of the proteinaceous compound. As detailed above, in addition to antibodies generated against full length proteins, antibodies also may be generated in response to smaller constructs comprising epitopic core regions, including wild-type and mutant epitopes. An epitope is an antigenic determinant. An antigen is any substance that is specifically recognized by an antibody or T-cell receptor. An immunogen is an antigen that induces a specific immune response.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (mAbs) are recognized to have certain advantages, e.g., reproducibility and large-scale production, and their use is generally preferred. The invention thus provides monoclonal antibodies of the human, murine, monkey, rat, hamster, rabbit and even chicken origin.

The term "antibody" is used to refer to any antibody-like molecule that has an antigen binding region, and includes antibody fragments such as Fab', Fab, $F(ab')_2$, single domain antibodies (DABs), Fv, scFv (single chain Fv), and the like. The techniques for preparing and using various antibody-based constructs and fragments are well known in the art. Means for preparing and characterizing antibodies are also well known in the art.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. Such antibodies are generally useful for in vivo therapeutic applications. This strategy reduces the host response to the foreign antibody and allows selection of the human effector functions.

III. Gelonin Polypeptides

Ribosome-inhibitory toxins (RITs) are potent inhibitors of protein synthesis in eukaryotes. The enzymatic domain of these proteins acts as a cytotoxic n-glycosidase that is able to inactivate catalytically ribosomes once they gain entry to the intracellular compartment. This is accomplished by cleaving the n-glycosidic bond of the adenine at position 4324 in the 28srRNA, which irreversibly inactivates the ribosome apparently by disrupting the binding site for elongation factors. RITs, which have been isolated from bacteria, are prevalent in higher plants. In plants, there are two types: Type I toxins possess a single polypeptide chain that has ribosome inhibiting activity, and Type II toxins have an A chain, comparable to the Type I protein, which is linked by a disulfide bond to a B chain possessing cell-binding properties. Examples of Type I RITs are gelonin, dodecandrin, tricosanthin, tricokirin, bryodin, mirabilis antiviral protein, barley ribosome-inactivating protein (BRIP), pokeweed antiviral proteins (PAPs), saporins, luffins, and momordins. Type II toxins include ricin and abrin. Toxins may be conjugated or expressed as a fusion protein with any of the polypeptides discussed herein. Alternatively, the modified toxins of the present invention may be conjugated to a small molecule, such as a chemotherapeutic or a targeting agent.

As described in the foregoing summary, certain aspects of the embodiments concern a cell targeting construct that comprises a designer Gelonin (dGel) polypeptide. In preferred aspects, a dGel polypeptide is a humanized polypeptide. One or more of the molecules for use in the current embodiments include, but are not limited to, FMH (SEQ ID NO: 1) comprising one or more of the following features: (a) a humanized antigen domain at the positions corresponding to Arg 25 through Pro 38; (b) a humanized antigen domain at the positions corresponding to Ser 72 through Lys 88; (c) a humanized antigen domain at the position corresponding to Arg 184 through Trp 198; (d) an amino acid substitution at the position corresponding to Phe 20; (e) an amino acid substitution at the position corresponding to Lys 24; (f) an amino acid substitution at the position corresponding to Tyr 78; (g) an amino acid substitution at the position corresponding to Tyr 85; (h) an amino acid substitution at the position corresponding to Tyr 95; (i) an amino acid substitution at the position corresponding to Phe 99; (j) an amino acid substitution at the position corresponding to Ile 177; (k) an amino acid substitution at the position corresponding to Ile 185; (l) an amino acid substitution at the position corresponding to Leu 201; and (m) an amino acid substitution at the position corresponding to Ile 205. For instance a dGel sequence for use according to the current embodiments may comprise a dGel polypeptide that at least 70%, 80%, 90%, 95%, 98% or more identical to FMH.

In additional aspects, dGel polypeptides may be further modified by one or more other amino substitutions while maintaining their enzymatic activity. For example, amino acid substitutions can be made at one or more positions wherein the substitution is for an amino acid having a similar hydrophilicity. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in dGel and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the dGel polypeptides described herein may be modified by the substitution of an amino acid, for different, but homologous amino acid with a similar hydrophilicity value. Amino acids with hydrophilicities within +/−1.0, or +/−0.5 points are considered homologous. Furthermore, it is envisioned that dGel sequences may be modified by amino acid deletions, substitutions, additions or insertions while retaining its enzymatic activity.

IV. Cell-Targeting Moieties

The toxins of the invention are particularly suited for use as components of cytotoxic therapeutic agents. These cytotoxic agents may be used in vivo to selectively eliminate a particular cell type to which the toxin component is targeted by the specific binding capacity of a second component. To form cytotoxic agents, modified toxins of the present invention may be conjugated to various cell targeting moieties, such as an antibody, a growth factor, a hormone, a peptide, an aptamer, or a cytokine. For instance, a cell targeting moiety according to the embodiments may bind to a vascular endothelial growth factor receptor. For example, the cell targeting moiety may be the 121-amino acid isoform of vascular endothelial growth factor ($VEGF_{121}$). Agents targeting the neovascularization process in tumors have significant potential for therapeutic impact. Molecules which interfere with the growth and development of vascular endothelial cells by targeting the VEGF/receptor complex have an additional advantage since these agents do not have to penetrate into the tumor parenchyma and the receptor targets are expressed on the luminal surface of tumor vascular endothelium.

In another aspect, there is provided a method of using the $VEGF_{121}$ fusion conjugate of the present invention to kill cells expressing type 2 VEGF receptors (kinase domain receptor/Flk-1 receptors). The $VEGF_{121}$ component of the conjugate binds to both VEGF receptor type 1 (Flt-1) and VEGF receptor type 2 (KDR/Flk-1) but is only internalized by cells expressing VEGF receptor type 2. In general, the conjugate is cytotoxic to cells expressing more than 2000 type 2 VEGF receptors per cell.

Possible binding of vascular endothelial growth factor-containing constructs to the neuropilin receptor could be a source of unwanted toxicity and mistargeting of the complex; however, it has been shown that the $VEGF_{121}$ fragment as opposed to other isoforms of VEGF-A does not appear to bind to this receptor.

In embodiments where the cell targeting moiety is an antibody, the antibodies may be monoclonal antibodies, including chimeric and CDR-grafted antibodies, antibody domains/fragments (e.g., Fab, Fab', F(ab').sub.2, single chain antibodies, and Fv or single variable domains), humanized antibodies, or human engineered antibodies. An immunotoxin may also consist of a fusion protein rather than an immunoconjugate.

The antibodies employed in the present invention as part of an immunotoxin may be targeted to any antigen. The antigen may be specific to an organism, to a cell type, to a disease or condition, or to a pathogen. Exemplary antigens include cell surface cellular proteins, for example tumor-associated antigens, viral proteins, microbial proteins, post-translational modifications or carbohydrates, and receptors, such as CD4 or CD8. Common tumor markers include carcinoembryonic antigen, prostate specific antigen, urinary tumor associated antigen, fetal antigen, tyrosinase (p97), gp68, gp240, TAG-72, HMFG, Sialyl Lewis Antigen, MucA, MucB, PLAP, estrogen receptor, Her-2/neu, laminin receptor, erb B and p155. Other antigens that may be targeted include the receptors for EGF and VEGF, TIE-1 and -2, CD-33, CD38, CD-20, CD-52, GP-240, Lym-1, MMO-2, and MMP-9.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example are the cell targeting agents described in U.S. Pat. Appln. No. 2004/005647 and in Winthrop et al., 2003 that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy.

The use of a region of a protein that mediates protein-protein interactions, including ligand-receptor interactions, also is contemplated by the present invention. This region could be used as an inhibitor or competitor of a protein-protein interaction or as a specific targeting motif Consequently, the invention covers using the targeting moiety to recruit the toxin or other therapeutic or diagnostic polypeptide to a particular body part, organ, tissue, or cell. Once the compositions of the present invention reach the particular area through the targeting motif, the toxin or other polypeptide can function.

Targeting moieties may take advantage of protein-protein interactions. These include interactions between and among proteins such as receptors and ligands; receptors and receptors; polymeric complexes; transcription factors; kinases and downstream targets; enzymes and substrates; etc. For example, a ligand binding domain mediates the protein:protein interaction between a ligand and its cognate receptor. Consequently, this domain could be used either to inhibit or compete with endogenous ligand binding or to target more specifically cell types that express a receptor that recognizes the ligand binding domain operatively attached to a therapeutic polypeptide, such as the gelonin toxin.

Examples of ligand binding domains include ligands such as VEGF/VPF; βFGF; αFGF; coagulation factors, and endothelial antigens necessary for angiogenesis (i.e., V3 integrin); growth factors such as transforming growth factor, fibroblast growth factor, colony stimulating factor, Kit ligand (KL), flk-2/flt-3, and platelet derived growth factor (PDGF) and PDGF family members; and ligands that bind to cell surface receptors such as MHC molecules, among others.

Extensively characterized ligands include asialoorosomucoid (ASOR) and transferrin. A synthetic neoglycoprotein, which recognizes the same receptor as ASOR, has been used as a gene delivery vehicle, and epidermal growth factor (EGF) has also been used to deliver genes to squamous carcinoma cells. Also, the human prostate-specific antigen may be used as the receptor for mediated delivery to prostate tissue. In still further embodiments, a lectin molecule may be used to target a compound to a cell expressing a particular carbohydrate on its surface.

Another class of compounds that is contemplated to be operatively linked to a therapeutic polypeptide, such as a toxin, includes interleukins and cytokines. A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)). Furthermore, the Fc portion of the heavy chain of an antibody may be used to target Fc receptor-expressing cells such as the use of the Fc portion of an IgE antibody to target mast cells and basophils.

V. Methods Of Making Modified Proteins And Designer Toxins

The present invention encompasses designer gelonin polypeptides that are less antigenic but that possesses activity that is comparable to a native protein.

The term "antigenic region" refers to a portion of a protein that is specifically recognized by an antibody or T-cell receptor. The term "less antigenic" means that a protein or region of a protein elicits a lower antibody response or is recognized by fewer antibodies (polyclonal) or the binding association with an antibody is reduced.

Antigenicity is relative to a particular organism. In many of the embodiments of the present invention, the organism is a human, but antigenicity may be discussed with respect to other organisms as well, such as other mammals-monkeys, gorillas, cows, rabbits, mice, sheep, cats, dogs, pigs, goats, etc., as well as avian organisms and any other organism that can elicit an immune response.

Once an antigenic region is identified, it may be removed, creating a truncated protein. Alternatively, the region may be replaced with a region believed to be less antigenic. The region may also be replaced with substitute amino acids. "Replaced" means that an amino acid at a particular position has been substituted with a different amino acid residue or with a modified amino acid. This may be accomplished by a number of ways. The region may be first removed and then the replacement region incorporated into a polynucleotide or the polypeptide. Recombinant DNA technology may be used to incorporate a particular coding region into a polynucleotide. Alternatively, an antigenic region may be mutagenized using site-specific mutagenesis techniques that are well known to those of ordinary skill in the art.

It is contemplated that amino acids flanking either side of an antigenic region may also be removed or replaced, either to facilitate the creation of a modified protein or to improve the protein in any way, such as decrease its antigenicity, increase the protein's stability, increase the activity of the protein, decrease the activity of the protein, etc. Furthermore, multiple amino acids may be replaced or removed from either antigenic region, flanking region, or both; thus, exactly or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 620, 640, 660, 680, 700, 720, 740, 760, 780, 800, 820, 840, 860, 880, 900, 920, 940, 960, 980, 1000, or more amino acids may be removed or replaced.

VI. Administration And Pharmaceutical Formulations

In some embodiments, an effective amount of a cell targeting construct is administered to a cell. In other embodiments, a therapeutically effective amount of the targeting construct is administered to an individual for the treatment of disease. The term "effective amount" as used herein is defined as the amount of the cell targeted dGel of the present embodiments that is necessary to result in a physiological change in the cell or tissue to which it is administered either when administered alone or in combination with a cytotoxic therapy. The term "therapeutically effective amount" as used herein is defined as the amount of the targeting molecule of the present embodiments that eliminate, decrease, delay, or minimize adverse effects of a disease, such as cancer. A skilled artisan readily recognizes that in many cases cell targeted dGel may not provide a cure but may only provide partial benefit, such as alleviation or improvement of at least one symptom. In some embodiments, a physiological change having some benefit is also considered therapeutically beneficial. Thus, in some embodiments, an amount of cell targeted dGel that provides a physiological change is considered an "effective amount" or a "therapeutically effective amount." It will additionally be clear that a therapeutically effective amount may be dependent upon the inclusion of additional therapeutic regimens tat administered concurrently or sequentially. Thus it will be understood that in certain embodiments a physical change may constitute an enhanced effectiveness of a second therapeutic treatment.

The cell targeting constructs of the embodiments may be administered to a subject per se or in the form of a pharmaceutical composition for the treatment of cancer, autoimmunity, transplantation rejection, post-traumatic immune responses and infectious diseases, for example by targeting viral antigens, such as gp120 of HIV. More specifically, the chimeric polypeptides may be useful in eliminating cells involved in immune cell-mediated disorder, including lymphoma; autoimmunity, transplantation rejection, graft-versus-host disease, ischemia and stroke. Pharmaceutical compositions comprising the proteins of the embodiments may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

In preferred embodiments, cancer cells may be treated by methods and compositions of the embodiments. Cancer cells that may be treated with cell targeting constructs according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma;

superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In preferred embodiments systemic formulations of the cell targeting constructs are contemplated. Systemic formulations include those designed for administration by injection, e.g., subcutaneous, intravenous, intramuscular, intrathecal or intraperitoneal injection, as well as those designed for transdermal, transmucosal, inhalation, oral or pulmonary administration. In the most preferred embodiments cell targeted dGel is delivered by direct intravenous or intratumoral injection.

For injection, the proteins of the embodiments may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

A. Effective Dosages

The cell targeted dGel of the embodiments will generally be used in an amount effective to achieve the intended purpose. For use to treat or prevent a disease condition, the molecules of the embodiments, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with dGel constructs of the embodiments include, but are not limited to, steroid and non-steroid anti-inflammatory agents.

B. Toxicity

Preferably, a therapeutically effective dose of the cell-targeted dGel described herein will provide therapeutic benefit without causing substantial toxicity.

Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition.

C. Pharmaceutical Preparations

Pharmaceutical compositions of the present embodiments comprise an effective amount of one or more chimeric polypeptides or chimeric polypeptides and at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The cell targeted dGel may comprise different types of carriers depending on whether it is to be administered in solid, liquid or aerosol form, and whether it need to be sterile for such routes of administration as injection. The present therapies of the embodiments can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present embodiments administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 5 mg/kg body weight to about 100 mg/kg body weight, about 5 microgram/kg body weight to about 500 mg/kg body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where compositions are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VII. Combination Therapies

In order to increase the effectiveness of a nucleic acid, polypeptide or nanoparticle complex of the present embodiments, it may be desirable to combine these compositions with other agents effective in the treatment of the disease of interest. It is contemplated that a wide variety of conditions or diseases may be treated, such as microbial pathogenesis, AIDS, autoimmune diseases, hyperproliferative disorders including cancers, leukemias, arthritis, inflammatory diseases, cardiovascular diseases and conditions, pathogenic diseases and conditions, and diabetes. The treatment of AIDS, cancer, and other hyperproliferative disorders is specifically contemplated.

As a non-limiting example, the treatment of cancer may be implemented with a dGel therapeutic of the present embodiments along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the anti-cancer peptide or nanoparticle complex and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the anti-cancer peptide or nanoparticle complex and the other includes the second agent(s). In particular embodiments, an anti-cancer peptide can be one agent, and an anti-cancer nanoparticle complex can be the other agent.

Treatment with the anti-cancer peptide or nanoparticle-complex may precede or follow the other agent treatment by intervals ranging from minutes to weeks. In embodiments where the other agent and the anti-cancer peptide or nanoparticle complex are applied separately to the cell, one would generally ensure that a significant period of time did not expire between the time of each delivery, such that the agent and the anti-cancer peptide or nanoparticle complex would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Various combinations may be employed, where the dGel-based therapy is "A" and the secondary agent, such as radiotherapy, chemotherapy or anti-inflammatory agent, is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | |
| A/B/A/B | A/B/B/A | B/B/A/A | B/A/B/A | B/A/A/B | |
| A/A/A/B | B/A/A/A | A/B/A/A | A/A/B/A | | |

In certain embodiments, administration of the dGel therapy of the present embodiments to a patient will follow general protocols for the administration of chemotherapeutics, taking into account the toxicity, if any. It is expected that the treatment cycles would be repeated as necessary. It also is contemplated that various standard therapies, as well as surgical intervention, may be applied in combination with the described hyperproliferative cell therapy.

Hyperproliferative diseases include cancer, for which there is a wide variety of treatment regimens such as anti-cancer agents or surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that therapy with modified proteins could be used similarly in conjunction with chemotherapeutic, radiotherapeutic, immunotherapeutic or other biological intervention, in addition to other pro-apoptotic or cell cycle regulating agents.

Alternatively, the gene therapy or protein administration of modified proteins may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

In some embodiments of the present invention, it is contemplated that a chemotherapeutic is operatively attached to a modified protein, such as a toxin molecule.

VIII. Examples

The following examples are included to demonstrate preferred embodiments of the embodiments. It should be appreciated by those of skill in the art that the techniques disclosed in the examples which follow represent techniques discovered by the inventor to function well in the practice of the embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction and Testing of Designer Gelonin-VEGF Fusion Constructs

Three different VEGF fusion constructs were generated using rGel and two deimmunized designer Gelonin (dGel) sequences, FMH and SDH (FIG. 1). The VEGF-rGel (SEQ ID NO: 6) construct was cloned into the pET32a vector (Novagen), which expresses a cleavable purification tag according to SEQ ID NO: 9. The VEGF-dGel constructs (SEQ ID NOs: 7 and 8) were each cloned into a modified pET32 vector, called pET32(T), that lacks the S tag coding sequence and expresses a cleavable purification tag according to SEQ ID NO: 10. The cloned constructs were transformed into AD494(DE3)pLysS bacteria (Novagen). The proteins were expressed and purified.

The functional activity of VEGF-FMH (SEQ ID NO: 3), VEGF-rGel (SEQ ID NO: 5), and rGel (SEQ ID NO: 11) were assayed using a cell-free protein translation inhibition assay kit from Amersham Pharmacia as described by the manufacturer. As determined by the rabbit reticulocyte translation assay, the purified VEGF-FMH, VEGF-rGel, and rGel had $IC_{50}$ values of 64 nM, 17.5 pM, and 11.8 pM, respectively, showing that humanization of rGel reduced the activity of the toxin by over three orders of magnitude (FIG. 2).

The fusion proteins were then used to treat transfected endothelial cells expressing the VEGFR-2 receptor (PAE-KDR) cell line to test for in vitro cytotoxic effects. Log-phase cells were seeded and allowed to attach overnight. Cells were further incubated with various concentrations of VEGF-Gelonin or rGel at 37° C. for 72 h. Cell viability was determined using the crystal violet staining method followed by solubilization of the dye in Sorenson's buffer as described previously (Cao et al., 2009).

Figure 3:
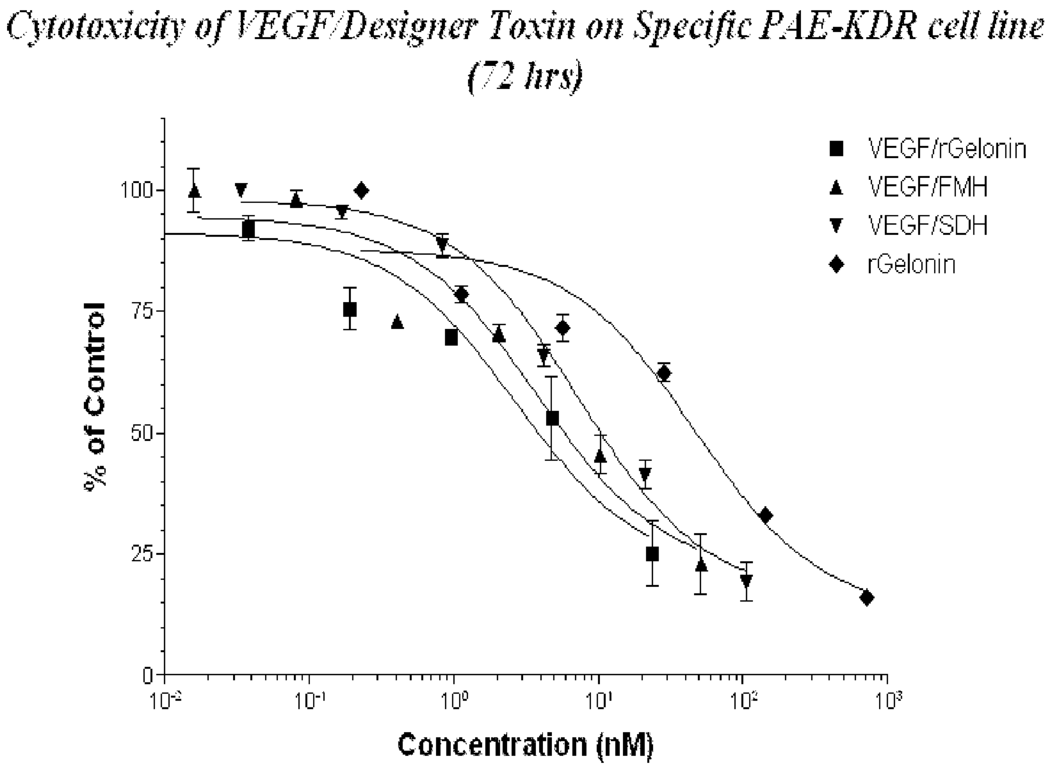
FIG. 3: Cytotoxicity of VEGF-Designer Toxin on specific PAE-KDR cell line. PAE-KDR cells were plated and allowed to attach overnight. After that, the cells were treated with different concentrations of toxins. After 72 h, the cells were stained with crystal violet.

The VEGF-Gelonin, VEGF-FMH, and VEGF-SDH (SEQ ID NO: 4) fusions demonstrated cytotoxicity to PAE-KDR cells with $IC_{50}$ values of 4, 6, and 11 nM, respectively (FIG. 3), and rGel demonstrated cytotoxic effects at somewhat higher doses (50 nM). Therefore, while the cell-free functional activity of the VEGF-FMH is reduced compared to the native rGel-VEGF fusion, the cytotoxicity is identical.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,680,338
U.S. Pat. No. 5,141,648
U.S. Pat. No. 5,563,250
U.S. Pat. No. 5,856,456
U.S. Pat. No. 5,880,270
U.S. Patent Appln. 2004/005647
Arai et al., Conformations of variably linked chimeric proteins evaluated by synchrotron X-ray small-angle scattering, *PROTEINS: Structure, Function, and Bioinformatics,* 57:829-838, 2004.
Cao et al., Construction and characterization of novel, recombinant immunotoxins targeting the Her2/neu oncogene product: in vitro and in vivo studies, *Cancer Res.,* 69:8987-8995, 2009.
Culver et al., In vivo gene transfer with retroviral vector-producing cells for treatment of experimental brain tumors, *Science,* 256:9575-9579, 1992.
Goyal et al., Inclusion of a furin-sensitive spacer enhances the cytotoxicity of ribotoxin restrictocin containing recombinant single-chain immunotoxins, *Biochem. J.,* 345:247-254, 2000.
Nechushtan et al., Adenocarcinoma cells are targeted by the new GnRH-PE66 chimeric toxin through specific gonadotropin-releasing hormone binding sites, *J. Biol. Chem.,* 272:11597-11603, 1997.
Onda et al., In vitro and in vivo cytotoxic activities of recombinant immunotoxin 8H9(Fv)-PE38 against breast cancer, osteosarcoma, and neuroblastoma, *Cancer Res.,* 64:1419-1424, 2004.
Remington's Pharmaceutical Sciences, 18th Ed. Mack Printing Company, 1990.
Robinson and Sauer, Optimizing the stability of single-chain proteins by linker length and composition mutagenesis, *Proc. Natl. Acad. Sci. USA,* 95:5929-5934, 1998.
Whitlow et al., An improved linker for single-chain Fv with reduced aggregation and enhanced proteolytic stability, *Prot. Eng.,* 6:989-995, 1993.
Winthrop et al., Selection and characterization of anti-MUC-1 scFvs intended for targeted therapy, *Clin. Cancer Res.,* 9:3845s-3853s, 2003.

What is claimed is:

1. A recombinant polypeptide comprising a recombinant gelonin toxin according to SEQ ID NO: 1 or SEQ ID NO: 2.

2. The polypeptide of claim 1, comprising the sequence of SEQ ID NO: 1.

3. The polypeptide of claim 1, comprising the sequence of SEQ ID NO: 2.

4. The polypeptide of claim 1, wherein the polypeptide is fused or conjugated to a second polypeptide.

5. The polypeptide of claim 4, wherein the second polypeptide and the recombinant gelonin toxin form a fusion protein and are separated by a linker.

6. The polypeptide of claim 5, wherein the linker is a G4S, (G4S)2, (G4S)3, 218 linker, enzymatically cleavable linker, or pH cleavable linker.

7. The polypeptide of claim 4, wherein the second polypeptide is a cell binding moiety.

8. The polypeptide of claim 7, wherein the cell binding moiety is an antibody or immunoglobulin chain.

9. The polypeptide of claim 8, wherein the antibody is a monoclonal antibody, human antibody, humanized antibody, deimmunized antibody, chimeric antibody, Fab', Fab, F(ab')2, single domain antibody, Fv, or single chain Fv (scFv) antibody.

10. The polypeptide of claim 7, wherein the cell binding moiety binds to a protein, carbohydrate, or lipid expressed on cancer cells.

11. The polypeptide of claim 7, wherein the cell binding moiety binds to BLyS, GP240, 5T4, HER1, HER2, CD-33, CD-38, Flt-1, Flk-1, CEA, FGFR3, IGFBP2, or IGF-1R.

12. The polypeptide of claim 11, wherein the cell binding moiety is $VEGF_{121}$.

13. The polypeptide of claim 12, comprising the sequence of SEQ ID NO: 3 or SEQ ID NO: 4.

14. A polynucleotide molecule comprising a nucleic acid sequence encoding a polypeptide of claim 1.

15. A host cell comprising the polynucleotide of claim 14.

16. The host cell of claim 15, wherein the host cell expresses the polypeptide.

17. The host cell of claim 15, wherein the host cell is a mammalian cell, a yeast cell, a bacterial cell, a ciliate cell, or an insect cell.

18. A composition comprising a polypeptide of claim 1.

19. The composition of claim 18, further comprising a pharmaceutically acceptable carrier.

20. A method of treating a cell proliferative disease in a subject comprising administering to the subject an effective amount of a polypeptide according to claim 1 comprising a recombinant gelonin and a cell binding moiety that specifically targets a diseased cell, thereby killing or inhibiting the diseased cell.

* * * * *

SEQUENCE LISTING

```
<160> NUMBER OF SEQ ID NOS: 23

<210> SEQ ID NO 1
<211> LENGTH: 251
<212> TYPE: PRT
<213> ORGANISM: Artificial Sequence
<220> FEATURE:
<223> OTHER INFORMATION: Artificial polypeptide

<400> SEQUENCE: 1

Gly Leu Asp Thr Val Ser Phe Ser Thr Lys Gly Ala Thr Tyr Ile Thr
1               5                   10                  15

Tyr Val Asn Ala Leu Asn Glu Leu Arg Val Lys Asn Gln Trp Asp Gly
            20                  25                  30

Thr Gln His Gly Val Glu Leu Leu Arg Lys Lys Cys Asp Asp Pro Gly
        35                  40                  45
```

-continued

```
Lys Cys Phe Val Leu Val Ala Leu Ser Asn Asp Asn Gly Gln Leu Ala
    50                  55                  60

Glu Ile Ala Ile Asp Val Thr Ser Ile Tyr Ile Val Gly Ile Gln Ala
65                  70                  75                  80

Arg Asn Glu Val Leu Phe Tyr Arg Asp Ala Pro Asp Ala Ala Phe Glu
                85                  90                  95

Gly Leu Gly Lys Asn Thr Ile Lys Thr Arg Leu His Phe Gly Gly Ser
            100                 105                 110

Tyr Pro Ser Leu Glu Gly Glu Lys Ala Tyr Arg Glu Thr Thr Asp Leu
        115                 120                 125

Gly Ile Glu Pro Leu Arg Ile Gly Ile Lys Lys Leu Asp Glu Asn Ala
    130                 135                 140

Ile Asp Asn Tyr Lys Pro Thr Glu Ile Ala Ser Ser Leu Leu Val Val
145                 150                 155                 160

Ile Gln Leu Val Ser Glu Ala Ala Arg Phe Thr Phe Ile Glu Asn Gln
                165                 170                 175

Leu Arg Asn Asn Phe Gln Gln Arg Val Ser Glu Glu Asn Glu Thr Thr
            180                 185                 190

Ser Tyr Glu Gly Lys Trp Gly Lys Leu Ser Phe Gln Ile Arg Thr Ser
        195                 200                 205

Gly Ala Asn Gly Met Phe Ser Glu Ala Val Glu Leu Glu Arg Ala Asn
    210                 215                 220

Gly Lys Lys Tyr Tyr Val Thr Ala Val Asp Gln Val Lys Pro Lys Ile
225                 230                 235                 240

Ala Leu Leu Lys Phe Val Asp Lys Asp Pro Lys
                245                 250


<210> SEQ ID NO 2
<211> LENGTH: 165
<212> TYPE: PRT
<213> ORGANISM: Artificial Sequence
<220> FEATURE:
<223> OTHER INFORMATION: Artificial polypeptide

<400> SEQUENCE: 2

Gly Leu Asp Thr Val Ser Phe Ser Thr Lys Arg Val Lys Asn Gln Trp
1               5                   10                  15

Asp Gly Thr Gln His Gly Val Glu Leu Leu Arg Lys Lys Cys Asp Asp
            20                  25                  30

Pro Gly Lys Cys Phe Val Leu Val Ala Leu Ser Asn Asp Asn Gly Gln
        35                  40                  45

Leu Ala Glu Ile Ala Ile Asp Val Thr Ser Ile Tyr Ile Val Gly Ile
    50                  55                  60

Gln Ala Arg Asn Glu Lys Leu Phe Tyr Arg Gly Gly Ser Tyr Pro Ser
65                  70                  75                  80

Leu Glu Gly Glu Lys Ala Tyr Arg Glu Thr Thr Asp Leu Gly Ile Glu
                85                  90                  95

Pro Leu Arg Ile Gly Ile Lys Lys Leu Asp Glu Asn Ala Ile Asp Asn
            100                 105                 110

Tyr Lys Pro Thr Glu Ile Ala Ser Ser Leu Leu Val Val Ile Gln Ser
        115                 120                 125

Val Ser Glu Ala Ala Arg Phe Thr Phe Ile Glu Asn Gln Leu Arg Asn
    130                 135                 140

Asn Phe Gln Gln Arg Val Ser Glu Glu Asn Glu Thr Thr Ser Tyr Glu
145                 150                 155                 160
```

```
Gly Lys Trp Gly Lys
                165


<210> SEQ ID NO 3
<211> LENGTH: 379
<212> TYPE: PRT
<213> ORGANISM: Artificial Sequence
<220> FEATURE:
<223> OTHER INFORMATION: Artificial polypeptide

<400> SEQUENCE: 3

Gly Ser Ala Pro Met Ala Glu Gly Gly Gly Gln Asn His His Glu Val
1               5                   10                  15

Val Lys Phe Met Asp Val Tyr Gln Arg Ser Tyr Cys His Pro Ile Glu
            20                  25                  30

Thr Leu Val Asp Ile Phe Gln Glu Tyr Pro Gly Glu Ile Glu Tyr Ile
        35                  40                  45

Phe Lys Pro Ser Cys Val Pro Leu Met Arg Cys Gly Gly Cys Cys Asn
    50                  55                  60

Asp Glu Gly Leu Glu Cys Val Pro Thr Glu Glu Ser Asn Ile Thr Met
65                  70                  75                  80

Gln Ile Met Arg Ile Lys Pro His Gln Gly Gln His Ile Gly Glu Met
                85                  90                  95

Ser Phe Leu Gln His Asn Lys Cys Glu Cys Arg Pro Lys Lys Asp Arg
            100                 105                 110

Ala Arg Gln Glu Lys Cys Asp Lys Pro Arg Arg Gly Gly Gly Gly Ser
        115                 120                 125

Gly Leu Asp Thr Val Ser Phe Ser Thr Lys Gly Ala Thr Tyr Ile Thr
    130                 135                 140

Tyr Val Asn Ala Leu Asn Glu Leu Arg Val Lys Asn Gln Trp Asp Gly
145                 150                 155                 160

Thr Gln His Gly Val Glu Leu Leu Arg Lys Lys Cys Asp Asp Pro Gly
                165                 170                 175

Lys Cys Phe Val Leu Val Ala Leu Ser Asn Asp Asn Gly Gln Leu Ala
            180                 185                 190

Glu Ile Ala Ile Asp Val Thr Ser Ile Tyr Ile Val Gly Ile Gln Ala
        195                 200                 205

Arg Asn Glu Val Leu Phe Tyr Arg Asp Ala Pro Asp Ala Ala Phe Glu
    210                 215                 220

Gly Leu Gly Lys Asn Thr Ile Lys Thr Arg Leu His Phe Gly Gly Ser
225                 230                 235                 240

Tyr Pro Ser Leu Glu Gly Glu Lys Ala Tyr Arg Glu Thr Thr Asp Leu
                245                 250                 255

Gly Ile Glu Pro Leu Arg Ile Gly Ile Lys Lys Leu Asp Glu Asn Ala
            260                 265                 270

Ile Asp Asn Tyr Lys Pro Thr Glu Ile Ala Ser Ser Leu Leu Val Val
        275                 280                 285

Ile Gln Leu Val Ser Glu Ala Ala Arg Phe Thr Phe Ile Glu Asn Gln
    290                 295                 300

Leu Arg Asn Asn Phe Gln Gln Arg Val Ser Glu Glu Asn Glu Thr Thr
305                 310                 315                 320

Ser Tyr Glu Gly Lys Trp Gly Lys Leu Ser Phe Gln Ile Arg Thr Ser
                325                 330                 335

Gly Ala Asn Gly Met Phe Ser Glu Ala Val Glu Leu Glu Arg Ala Asn
            340                 345                 350
```

```
Gly Lys Lys Tyr Tyr Val Thr Ala Val Asp Gln Val Lys Pro Lys Ile
        355                 360                 365

Ala Leu Leu Lys Phe Val Asp Lys Asp Pro Lys
    370                 375


<210> SEQ ID NO 4
<211> LENGTH: 293
<212> TYPE: PRT
<213> ORGANISM: Artificial Sequence
<220> FEATURE:
<223> OTHER INFORMATION: Artificial polypeptide

<400> SEQUENCE: 4

Gly Ser Ala Pro Met Ala Glu Gly Gly Gly Gln Asn His His Glu Val
1               5                   10                  15

Val Lys Phe Met Asp Val Tyr Gln Arg Ser Tyr Cys His Pro Ile Glu
            20                  25                  30

Thr Leu Val Asp Ile Phe Gln Glu Tyr Pro Gly Glu Ile Glu Tyr Ile
        35                  40                  45

Phe Lys Pro Ser Cys Val Pro Leu Met Arg Cys Gly Gly Cys Cys Asn
    50                  55                  60

Asp Glu Gly Leu Glu Cys Val Pro Thr Glu Glu Ser Asn Ile Thr Met
65                  70                  75                  80

Gln Ile Met Arg Ile Lys Pro His Gln Gly Gln His Ile Gly Glu Met
                85                  90                  95

Ser Phe Leu Gln His Asn Lys Cys Glu Cys Arg Pro Lys Lys Asp Arg
            100                 105                 110

Ala Arg Gln Glu Lys Cys Asp Lys Pro Arg Arg Gly Gly Gly Gly Ser
        115                 120                 125

Gly Leu Asp Thr Val Ser Phe Ser Thr Lys Arg Val Lys Asn Gln Trp
    130                 135                 140

Asp Gly Thr Gln His Gly Val Glu Leu Leu Arg Lys Lys Cys Asp Asp
145                 150                 155                 160

Pro Gly Lys Cys Phe Val Leu Val Ala Leu Ser Asn Asp Asn Gly Gln
                165                 170                 175

Leu Ala Glu Ile Ala Ile Asp Val Thr Ser Ile Tyr Ile Val Gly Ile
            180                 185                 190

Gln Ala Arg Asn Glu Lys Leu Phe Tyr Arg Gly Gly Ser Tyr Pro Ser
        195                 200                 205

Leu Glu Gly Glu Lys Ala Tyr Arg Glu Thr Thr Asp Leu Gly Ile Glu
    210                 215                 220

Pro Leu Arg Ile Gly Ile Lys Lys Leu Asp Glu Asn Ala Ile Asp Asn
225                 230                 235                 240

Tyr Lys Pro Thr Glu Ile Ala Ser Ser Leu Leu Val Val Ile Gln Ser
                245                 250                 255

Val Ser Glu Ala Ala Arg Phe Thr Phe Ile Glu Asn Gln Leu Arg Asn
            260                 265                 270

Asn Phe Gln Gln Arg Val Ser Glu Glu Asn Glu Thr Thr Ser Tyr Glu
        275                 280                 285

Gly Lys Trp Gly Lys
    290


<210> SEQ ID NO 5
<211> LENGTH: 379
<212> TYPE: PRT
<213> ORGANISM: Artificial Sequence
<220> FEATURE:
```

<223> OTHER INFORMATION: Artificial polypeptide

<400> SEQUENCE: 5

Ala Met Thr Pro Met Ala Glu Gly Gly Gly Gln Asn His His Glu Val
1 5 10 15

Val Lys Phe Met Asp Val Tyr Gln Arg Ser Tyr Cys His Pro Ile Glu
20 25 30

Thr Leu Val Asp Ile Phe Gln Glu Tyr Pro Gly Glu Ile Glu Tyr Ile
35 40 45

Phe Lys Pro Ser Cys Val Pro Leu Met Arg Cys Gly Gly Cys Cys Asn
50 55 60

Asp Glu Gly Leu Glu Cys Val Pro Thr Glu Glu Ser Asn Ile Thr Met
65 70 75 80

Gln Ile Met Arg Ile Lys Pro His Gln Gly Gln His Ile Gly Glu Met
85 90 95

Ser Phe Leu Gln His Asn Lys Cys Glu Cys Arg Pro Lys Lys Asp Arg
100 105 110

Ala Arg Gln Glu Lys Cys Asp Lys Pro Arg Arg Gly Gly Gly Gly Ser
115 120 125

Gly Leu Asp Thr Val Ser Phe Ser Thr Lys Gly Ala Thr Tyr Ile Thr
130 135 140

Tyr Val Asn Phe Leu Asn Glu Leu Arg Val Lys Leu Lys Pro Glu Gly
145 150 155 160

Asn Ser His Gly Ile Pro Leu Leu Arg Lys Lys Cys Asp Asp Pro Gly
165 170 175

Lys Cys Phe Val Leu Val Ala Leu Ser Asn Asp Asn Gly Gln Leu Ala
180 185 190

Glu Ile Ala Ile Asp Val Thr Ser Val Tyr Val Val Gly Tyr Gln Val
195 200 205

Arg Asn Arg Ser Tyr Phe Phe Lys Asp Ala Pro Asp Ala Ala Tyr Glu
210 215 220

Gly Leu Phe Lys Asn Thr Ile Lys Thr Gly Leu His Phe Gly Gly Ser
225 230 235 240

Tyr Pro Ser Leu Glu Gly Glu Lys Ala Tyr Arg Glu Thr Thr Asp Leu
245 250 255

Gly Ile Glu Pro Leu Arg Ile Gly Ile Lys Lys Leu Asp Glu Asn Ala
260 265 270

Ile Asp Asn Tyr Lys Pro Thr Glu Ile Ala Ser Ser Leu Leu Val Val
275 280 285

Ile Gln Met Val Ser Glu Ala Ala Arg Phe Thr Phe Ile Glu Asn Gln
290 295 300

Ile Arg Asn Asn Phe Gln Gln Arg Ile Arg Pro Ala Asn Asn Thr Ile
305 310 315 320

Ser Leu Glu Asn Lys Trp Gly Lys Leu Ser Phe Gln Ile Arg Thr Ser
325 330 335

Gly Ala Asn Gly Met Phe Ser Glu Ala Val Glu Leu Glu Arg Ala Asn
340 345 350

Gly Lys Lys Tyr Tyr Val Thr Ala Val Asp Gln Val Lys Pro Lys Ile
355 360 365

Ala Leu Leu Lys Phe Val Asp Lys Asp Pro Lys
370 375

<210> SEQ ID NO 6
<211> LENGTH: 1137

-continued

<212> TYPE: DNA
<213> ORGANISM: Artificial Sequence
<220> FEATURE:
<223> OTHER INFORMATION: Artificial polynucleotide

<400> SEQUENCE: 6
gccatgacac ccatggcaga aggaggaggg cagaatcatc acgaagtggt gaagttcatg 60
gatgtctatc agcgcagcta ctgccatcca atcgagaccc tggtggacat cttccaggag 120
taccctggtg agatcgagta catcttcaag ccatcctgtg tgcccctgat gcgatgcggg 180
ggctgctgca atgacgaggg cctggagtgt gtgcccactg aggagtccaa catcaccatg 240
cagattatgc ggatcaaacc tcaccaaggc cagcacatag gagagatgag cttcctacag 300
cacaacaaat gtgaatgcag accaaagaaa gatagagcaa gacaagaaaa atgtgacaag 360
ccgaggcggg gtggcggtgg ctccggtcta gacaccgtga gctttagcac taaaggtgcc 420
acttatatta cctacgtgaa tttcttgaat gagctacgag ttaaattgaa acccgaaggt 480
aacagccatg gaatcccatt gctgcgcaaa aaatgtgatg atcctggaaa gtgtttcgtt 540
ttggtagcgc tttcaaatga caatggacag ttggcggaaa tagctataga tgttacaagt 600
gtttatgtgg tgggctatca agtaagaaac agatcttact tctttaaaga tgctccagat 660
gctgcttacg aaggcctctt caaaaacaca attaaaacag gacttcattt tggcggcagc 720
tatccctcgc tggaaggtga gaaggcatat agagagacaa cagacttggg cattgaacca 780
ttaaggattg gcatcaagaa acttgatgaa aatgcgatag acaattataa accaacggag 840
atagctagtt ctctattggt tgttattcaa atggtgtctg aagcagctcg attcaccttt 900
attgagaacc aaattagaaa taactttcaa cagagaattc gcccggcgaa taatacaatc 960
agccttgaga ataaatgggg taaactctcg ttccagatcc ggacatcagg tgcaaatgga 1020
atgttttcgg aggcagttga attggaacgt gcaaatggca aaaaatacta cgtcaccgca 1080
gttgatcaag taaaacccaa aatagcactc ttgaagttcg tcgataaaga tcctaaa 1137

<210> SEQ ID NO 7
<211> LENGTH: 1137
<212> TYPE: DNA
<213> ORGANISM: Artificial Sequence
<220> FEATURE:
<223> OTHER INFORMATION: Artificial polynucleotide

<400> SEQUENCE: 7
ggcagcgcac ccatggcaga aggaggaggg cagaatcatc acgaagtggt gaagttcatg 60
gatgtctatc agcgcagcta ctgccatcca atcgagaccc tggtggacat cttccaggag 120
taccctggtg agatcgagta catcttcaag ccatcctgtg tgcccctgat gcgatgcggg 180
ggctgctgca atgacgaggg cctggagtgt gtgcccactg aggagtccaa catcaccatg 240
cagattatgc ggatcaaacc tcaccaaggc cagcacatag gagagatgag cttcctacag 300
cacaacaaat gtgaatgcag accaaagaaa gatagagcaa gacaagaaaa atgtgacaag 360
ccgaggcggg gtggcggtgg ctccggtcta gataccgtgt cattctcgac gaaaggcgcc 420
acctacatta cctacgtgaa cgctctgaac gaactgcgtg tcaaaaacca atgggatggc 480
acccagcatg gtgtggaact gctgcgtaaa aaatgcgatg acccgggcaa atgttttgtc 540
ctggtggcgc tgagtaacga taatggtcag ctggcggaaa ttgccatcga cgttacctca 600
atttatatcg tcggcatcca agcgcgtaac gaagttctgt tttaccgtga tgcaccggat 660
gccgcatttg aaggcctggg taaaaatacc attaaaacgc gtctgcactt cggcggtagt 720

-continued

```
tatccgtccc tggaaggtga aaaagcctac cgtgaaacca cggatctggg catcgaaccg    780

ctgcgcattg gtatcaaaaa actggatgaa aacgcaattg acaattataa accgaccgaa    840

atcgcgagca gcctgctggt tgtgattcag ctggtcagcg aagcagctcg ctttacgttc    900

atcgaaaacc aactgcgtaa caattttcag caacgcgtta gcgaagaaaa tgaaaccacg    960

tcttacgaag gcaaatgggg taaactgtca tttcagattc gtacctcggg cgcgaacggc   1020

atgttctccg aagcagtgga actggaacgc gctaatggca aaaaatatta cgttacggcc   1080

gttgaccagg tgaaaccgaa aatcgcactg ctgaaatttg tggataaaga cccgaaa      1137
```

<210> SEQ ID NO 8
<211> LENGTH: 879
<212> TYPE: DNA
<213> ORGANISM: Artificial Sequence
<220> FEATURE:
<223> OTHER INFORMATION: Artificial polynucleotide

<400> SEQUENCE: 8

```
ggcagcgcac ccatggcaga aggaggaggg cagaatcatc acgaagtggt gaagttcatg     60

gatgtctatc agcgcagcta ctgccatcca atcgagaccc tggtggacat cttccaggag    120

taccctggtg agatcgagta catcttcaag ccatcctgtg tgcccctgat gcgatgcggg    180

ggctgctgca atgacgaggg cctggagtgt gtgcccactg aggagtccaa catcaccatg    240

cagattatgc ggatcaaacc tcaccaaggc cagcacatag gagagatgag cttcctacag    300

cacaacaaat gtgaatgcag accaaagaaa gatagagcaa gacaagaaaa atgtgacaag    360

ccgaggcggg gtggcggtgg ctccggtcta gataccgtct ccttctcaac caaacgtgtg    420

aaaaatcaat gggatggcac ccaacatggc gtggaactgc tgcgtaaaaa atgcgatgac    480

ccgggcaaat gttttgtcct ggtggcactg agcaacgata atggtcagct ggcagaaatt    540

gctatcgacg ttaccagtat ttatatcgtc ggcatccaag cacgtaacga aaaactgttc    600

tatcgcggcg gttcataccc gtcgctggaa ggtgaaaaag cgtatcgtga aaccacggat    660

ctgggcattg aaccgctgcg cattggtatc aaaaaactgg atgaaaacgc gattgacaat    720

tacaaaccga ccgaaatcgc gagcagcctg ctggttgtga ttcagagtgt gtccgaagcg    780

gcccgtttta cgttcatcga aaatcaactg cgcaacaatt tccaacagcg tgtgagcgaa    840

gaaaatgaaa ccacctcgta tgaaggcaaa tggggcaaa                           879
```

<210> SEQ ID NO 9
<211> LENGTH: 158
<212> TYPE: PRT
<213> ORGANISM: Artificial Sequence
<220> FEATURE:
<223> OTHER INFORMATION: Artificial polypeptide

<400> SEQUENCE: 9

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80
```

```
Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys
145                 150                 155


<210> SEQ ID NO 10
<211> LENGTH: 129
<212> TYPE: PRT
<213> ORGANISM: Artificial Sequence
<220> FEATURE:
<223> OTHER INFORMATION: Artificial polypeptide

<400> SEQUENCE: 10

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg


<210> SEQ ID NO 11
<211> LENGTH: 251
<212> TYPE: PRT
<213> ORGANISM: Artificial Sequence
<220> FEATURE:
<223> OTHER INFORMATION: Artificial polypeptide

<400> SEQUENCE: 11

Gly Leu Asp Thr Val Ser Phe Ser Thr Lys Gly Ala Thr Tyr Ile Thr
1               5                   10                  15

Tyr Val Asn Phe Leu Asn Glu Leu Arg Val Lys Leu Lys Pro Glu Gly
            20                  25                  30

Asn Ser His Gly Ile Pro Leu Leu Arg Lys Lys Cys Asp Asp Pro Gly
        35                  40                  45

Lys Cys Phe Val Leu Val Ala Leu Ser Asn Asp Asn Gly Gln Leu Ala
    50                  55                  60

Glu Ile Ala Ile Asp Val Thr Ser Val Tyr Val Val Gly Tyr Gln Val
65                  70                  75                  80

Arg Asn Arg Ser Tyr Phe Phe Lys Asp Ala Pro Asp Ala Ala Tyr Glu
                85                  90                  95
```

-continued

```
Gly Leu Phe Lys Asn Thr Ile Lys Thr Gly Leu His Phe Gly Gly Ser
            100                 105                 110

Tyr Pro Ser Leu Glu Gly Glu Lys Ala Tyr Arg Glu Thr Thr Asp Leu
        115                 120                 125

Gly Ile Glu Pro Leu Arg Ile Gly Ile Lys Lys Leu Asp Glu Asn Ala
    130                 135                 140

Ile Asp Asn Tyr Lys Pro Thr Glu Ile Ala Ser Ser Leu Leu Val Val
145                 150                 155                 160

Ile Gln Met Val Ser Glu Ala Ala Arg Phe Thr Phe Ile Glu Asn Gln
                165                 170                 175

Ile Arg Asn Asn Phe Gln Gln Arg Ile Arg Pro Ala Asn Asn Thr Ile
            180                 185                 190

Ser Leu Glu Asn Lys Trp Gly Lys Leu Ser Phe Gln Ile Arg Thr Ser
        195                 200                 205

Gly Ala Asn Gly Met Phe Ser Glu Ala Val Glu Leu Glu Arg Ala Asn
    210                 215                 220

Gly Lys Lys Tyr Tyr Val Thr Ala Val Asp Gln Val Lys Pro Lys Ile
225                 230                 235                 240

Ala Leu Leu Lys Phe Val Asp Lys Asp Pro Lys
                245                 250


<210> SEQ ID NO 12
<211> LENGTH: 316
<212> TYPE: PRT
<213> ORGANISM: Gelonium multiflorum

<400> SEQUENCE: 12

Met Lys Gly Asn Met Lys Val Tyr Trp Ile Lys Ile Ala Val Ala Thr
1               5                   10                  15

Trp Phe Cys Cys Thr Thr Ile Val Leu Gly Ser Thr Ala Arg Ile Phe
            20                  25                  30

Ser Leu Pro Thr Asn Asp Glu Glu Glu Thr Ser Lys Thr Leu Gly Leu
        35                  40                  45

Asp Thr Val Ser Phe Ser Thr Lys Gly Ala Thr Tyr Ile Thr Tyr Val
    50                  55                  60

Asn Phe Leu Asn Glu Leu Arg Val Lys Leu Lys Pro Glu Gly Asn Ser
65                  70                  75                  80

His Gly Ile Pro Leu Leu Arg Lys Lys Cys Asp Asp Pro Gly Lys Cys
                85                  90                  95

Phe Val Leu Val Ala Leu Ser Asn Asp Asn Gly Gln Leu Ala Glu Ile
            100                 105                 110

Ala Ile Asp Val Thr Ser Val Tyr Val Val Gly Tyr Gln Val Arg Asn
        115                 120                 125

Arg Ser Tyr Phe Phe Lys Asp Ala Pro Asp Ala Ala Tyr Glu Gly Leu
    130                 135                 140

Phe Lys Asn Thr Ile Lys Thr Arg Leu His Phe Gly Gly Ser Tyr Pro
145                 150                 155                 160

Ser Leu Glu Gly Glu Lys Ala Tyr Arg Glu Thr Thr Asp Leu Gly Ile
                165                 170                 175

Glu Pro Leu Arg Ile Gly Ile Lys Lys Leu Asp Glu Asn Ala Ile Asp
            180                 185                 190

Asn Tyr Lys Pro Thr Glu Ile Ala Ser Ser Leu Leu Val Val Ile Gln
        195                 200                 205

Met Val Ser Glu Ala Ala Arg Phe Thr Phe Ile Glu Asn Gln Ile Arg
    210                 215                 220
```

Asn Asn Phe Gln Gln Arg Ile Arg Pro Ala Asn Asn Thr Ile Ser Leu
225 230 235 240

Glu Asn Lys Trp Gly Lys Leu Ser Phe Gln Ile Arg Thr Ser Gly Ala
245 250 255

Asn Gly Met Phe Ser Glu Ala Val Glu Leu Glu Arg Ala Asn Gly Lys
260 265 270

Lys Tyr Tyr Val Thr Ala Val Asp Gln Val Lys Pro Lys Ile Ala Leu
275 280 285

Leu Lys Phe Val Asp Lys Asp Pro Lys Thr Ser Leu Ala Ala Glu Leu
290 295 300

Ile Ile Gln Asn Tyr Glu Ser Leu Val Gly Phe Asp
305 310 315

<210> SEQ ID NO 13
<211> LENGTH: 18
<212> TYPE: PRT
<213> ORGANISM: Artificial Sequence
<220> FEATURE:
<223> OTHER INFORMATION: Artificial polypeptide

<400> SEQUENCE: 13

Gly Ser Thr Ser Gly Ser Gly Lys Pro Gly Ser Gly Glu Gly Ser Thr
1 5 10 15

Lys Gly

<210> SEQ ID NO 14
<211> LENGTH: 5
<212> TYPE: PRT
<213> ORGANISM: Artificial Sequence
<220> FEATURE:
<223> OTHER INFORMATION: Artificial polypeptide

<400> SEQUENCE: 14

Glu Ala Ala Ala Lys
1 5

<210> SEQ ID NO 15
<211> LENGTH: 5
<212> TYPE: PRT
<213> ORGANISM: Artificial Sequence
<220> FEATURE:
<223> OTHER INFORMATION: Artificial polypeptide

<400> SEQUENCE: 15

Gly Gly Gly Gly Ser
1 5

<210> SEQ ID NO 16
<211> LENGTH: 16
<212> TYPE: PRT
<213> ORGANISM: Artificial Sequence
<220> FEATURE:
<223> OTHER INFORMATION: Artificial polypeptide

<400> SEQUENCE: 16

Arg Gln Ile Lys Ile Trp Phe Gln Asn Arg Arg Met Lys Trp Lys Lys
1 5 10 15

<210> SEQ ID NO 17
<211> LENGTH: 26
<212> TYPE: PRT
<213> ORGANISM: Artificial Sequence
<220> FEATURE:

<223> OTHER INFORMATION: Artificial polypeptide

<400> SEQUENCE: 17

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 18
<211> LENGTH: 13
<212> TYPE: PRT
<213> ORGANISM: Artificial Sequence
<220> FEATURE:
<223> OTHER INFORMATION: Artificial polypeptide

<400> SEQUENCE: 18

```
Gly Arg Lys Lys Arg Arg Gln Arg Arg Arg Pro Pro Gln
1               5                   10
```

<210> SEQ ID NO 19
<211> LENGTH: 10
<212> TYPE: PRT
<213> ORGANISM: Artificial Sequence
<220> FEATURE:
<223> OTHER INFORMATION: Artificial polypeptide

<400> SEQUENCE: 19

```
Thr Lys Ile Glu Ser Leu Lys Glu His Gly
1               5                   10
```

<210> SEQ ID NO 20
<211> LENGTH: 10
<212> TYPE: PRT
<213> ORGANISM: Artificial Sequence
<220> FEATURE:
<223> OTHER INFORMATION: Artificial polypeptide

<400> SEQUENCE: 20

```
Thr Gln Ile Glu Asn Leu Lys Glu Lys Gly
1               5                   10
```

<210> SEQ ID NO 21
<211> LENGTH: 25
<212> TYPE: PRT
<213> ORGANISM: Artificial Sequence
<220> FEATURE:
<223> OTHER INFORMATION: Artificial polypeptide

<400> SEQUENCE: 21

```
Gly Leu Phe Glu Ala Ile Glu Gly Phe Ile Glu Asn Gly Trp Glu Gly
1               5                   10                  15

Met Ile Glu Gly Trp Tyr Gly Cys Gly
            20                  25
```

<210> SEQ ID NO 22
<211> LENGTH: 26
<212> TYPE: PRT
<213> ORGANISM: Artificial Sequence
<220> FEATURE:
<223> OTHER INFORMATION: Artificial polypeptide

<400> SEQUENCE: 22

```
Ala Ala Leu Glu Ala Leu Ala Glu Ala Leu Glu Ala Leu Ala Glu Ala
1               5                   10                  15
```

-continued

```
Leu Glu Ala Leu Ala Glu Ala Ala Ala Ala
            20                  25


<210> SEQ ID NO 23
<211> LENGTH: 1176
<212> TYPE: DNA
<213> ORGANISM: Gelonium multiflorum

<400> SEQUENCE: 23

cagcttctca cttgtttggg ataatgaaag ggaacatgaa ggtgtactgg attaagattg      60

ctgtggcgac atggttttgc tgcactacta ttgtacttgg atcaacggcg aggattttct     120

ctcttcccac aaatgatgaa gaagaaacca gtaagacgct tggcctggac accgtgagct     180

ttagcactaa aggtgccact tatattacct acgtgaattt cttgaatgag ctacgagtta     240

aattgaaacc cgaaggtaac agccatggaa tcccattgct gcgcaaaaaa tgtgatgatc     300

ctggaaagtg tttcgttttg gtagcgcttt caaatgacaa tggacagttg gcggaaatag     360

ctatagatgt tacaagtgtt tatgtggtgg gctatcaagt aagaaacaga tcttacttct     420

ttaaagatgc tccagatgct gcttacgaag gcctcttcaa aaacacaatt aaaacaagac     480

ttcattttgg cggcagctat ccctcgctgg aaggtgagaa ggcatataga gagacaacag     540

acttgggcat tgaaccatta aggattggca tcaagaaact tgatgaaaat gcgatagaca     600

attataaacc aacggagata gctagttctc tattggttgt tattcaaatg gtgtctgaag     660

cagctcgatt cacctttatt gagaaccaaa ttagaaataa ctttcaacag agaattcgcc     720

cggcgaataa tacaatcagc cttgagaata aatggggtaa actctcgttc cagatccgga     780

catcaggtgc aaatggaatg ttttcggagg cagttgaatt ggaacgtgca aatggcaaaa     840

aatactatgt caccgcagtt gatcaagtaa aacccaaaat agcactcttg aagttcgtcg     900

ataaagatcc taaaacgagc cttgctgctg aattgataat ccagaactat gagtcattag     960

tgggctttga ttagtacaac ttattgtgct ttttatatat tatagatatg atgccgggcc    1020

atgtattggc cttcgtagct taaataaagg catcgaatat tagcctcggt ggtgtatcta    1080

tcatgctgtg ttgtaaaact gccaatgttt atgttatcaa acagaaattg gcatgaagtt    1140

tctgtacaag tgttcaataa actgggctat acatgc                              1176
```